US009289625B2

(12) United States Patent
Fisher et al.

(10) Patent No.: US 9,289,625 B2
(45) Date of Patent: *Mar. 22, 2016

(54) BRACHYTHERAPY SEED WITH FAST DISSOLVING MATRIX FOR OPTIMAL DELIVERY OF RADIONUCLIDES TO CANCER TISSUE

(71) Applicants: Battelle Memorial Institute, Richland, WA (US); University of Utah Research Foundation, Salt Lake City, UT (US)

(72) Inventors: Darrell R. Fisher, Richland, WA (US); You Han Bae, Salt Lake City, UT (US); Zhonggao Gao, Salt Lake City, UT (US)

(73) Assignees: Battelle Memorial Institute, Richland, WA (US); University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/454,605

(22) Filed: Aug. 7, 2014

(65) Prior Publication Data
US 2014/0350326 A1 Nov. 27, 2014

Related U.S. Application Data

(63) Continuation of application No. 12/552,190, filed on Sep. 1, 2009, now Pat. No. 8,821,364, which is a continuation-in-part of application No. 12/202,954, filed on Sep. 2, 2008, now abandoned.

(51) Int. Cl.
*A61N 5/10* (2006.01)
*A61K 9/00* (2006.01)
(Continued)

(52) U.S. Cl.
CPC ............ *A61N 5/1001* (2013.01); *A61B 19/54* (2013.01); *A61K 9/0024* (2013.01);
(Continued)

(58) Field of Classification Search
CPC ...... A61N 5/10; A61N 5/1001; A61N 5/1002; A61N 5/1007; A61N 5/1014–5/1017; A61N 5/1027; A61N 5/1028
USPC ........................................................ 600/1–8
See application file for complete search history.

(56) References Cited

U.S. PATENT DOCUMENTS

| 6,248,057 B1 * | 6/2001 | Mavity et al. ................... 600/3 |
| 6,589,502 B1 | 7/2003 | Coniglione et al. |

(Continued)

FOREIGN PATENT DOCUMENTS

| WO | WO 97/33628 | 9/1997 |
| WO | WO 00/51136 | 8/2000 |

(Continued)

OTHER PUBLICATIONS

WO PCT/US09/055738SearchReport, Nov. 24, 2009, Battelle Memorial Institute.
(Continued)

*Primary Examiner* — Charles A Marmor, II
*Assistant Examiner* — Carrie R Dorna
(74) *Attorney, Agent, or Firm* — Wells St. John P.S.

(57) ABSTRACT

A system, method and device for treating tumor cells utilizing a resorbable therapy seed made up of microspheres containing a beta- or alpha-particle-emitting radiation source and a resorbable polymer matrix. These seeds are implanted within the tumor and then rapidly dissolved so as to release the microspheres from the polymer matrix. These microspheres then spread within a preselected target area and provide radiation therapy in a predetermined amount and at a preselected rate according the specific needs and necessities of the users. The configuration of the microspheres, the types of radiation provided and the location and use of these microspheres provides desired localized treatment to target cells while preferentially avoiding or minimizing undesired damage to surrounding tissue. The present invention provides a method for making the seeds, as well as a method for utilizing the seeds as a part of the treatment method.

19 Claims, 4 Drawing Sheets

(51) Int. Cl.

| | |
|---|---|
| *A61K 9/16* | (2006.01) |
| *A61K 51/06* | (2006.01) |
| *A61K 51/12* | (2006.01) |
| *A61B 19/00* | (2006.01) |

(52) U.S. Cl.
 CPC .............. *A61K 9/1647* (2013.01); *A61K 51/06* (2013.01); *A61K 51/1251* (2013.01); *A61B 2019/5466* (2013.01); *A61N 2005/1024* (2013.01); *A61N 2005/1087* (2013.01); *A61N 2005/1089* (2013.01)

(56) References Cited

U.S. PATENT DOCUMENTS

| | | | |
|---|---|---|---|
| 6,666,811 | B1 * | 12/2003 | Good ................................ 600/8 |
| 6,746,661 | B2 * | 6/2004 | Kaplan ........................ 424/1.25 |
| 6,841,617 | B2 | 1/2005 | Jeong et al. |
| 6,869,588 | B2 | 3/2005 | Weller et al. |
| 6,986,880 | B2 | 1/2006 | Coniglione et al. |
| 7,087,244 | B2 | 8/2006 | Jeong et al. |
| 7,229,973 | B2 | 6/2007 | Bae et al. |
| 7,371,781 | B2 | 5/2008 | Bae et al. |
| 2002/0173451 | A1 * | 11/2002 | Yao et al. ........................... 514/8 |
| 2003/0088140 | A1 | 5/2003 | Terwilliger et al. |
| 2004/0197264 | A1 | 10/2004 | Schwarz et al. |
| 2004/0228794 | A1 * | 11/2004 | Weller et al. .................. 424/1.11 |
| 2005/0186263 | A1 | 8/2005 | Bae et al. |
| 2006/0269587 | A1 | 11/2006 | Iversen et al. |
| 2008/0187998 | A1 | 8/2008 | Kang et al. |
| 2008/0213379 | A1 | 9/2008 | Bae et al. |
| 2009/0060955 | A1 | 3/2009 | Bae et al. |
| 2009/0274753 | A1 | 11/2009 | Bae et al. |

FOREIGN PATENT DOCUMENTS

| | | |
|---|---|---|
| WO | WO 2004/026111 | 4/2004 |
| WO | WO 2005/087274 | 9/2005 |
| WO | WO 2009/029935 | 3/2009 |
| WO | PCT/US09/055738 | 3/2011 |

OTHER PUBLICATIONS

WO PCT/US09/055738WrittenOpinion, Nov. 24, 2009, Battelle Memorial Institute.

Atassi, Bassel, et al., "Billary Sequalae Following Radioemolization with Yttrium-90 Microspheres", Journal of Vascular and Intgerventional Radiology, VA, May 1, 2008, pp. 691-697.

Lee, Eun Seong, et al., "Doxorubicin Loaded pH-Sensitive Polymeric Micelles for Reversal of Resistant MCF-7 Tumor", Journal of Controlled Release, 103, 2005, pp. 405-418.

Lee, Eun Seong, et al., "Super pH-Sensitive Multifunctional Polymeric Micelle", Nano Letters, 5 (2), Jan. 25, 2005, pp. 325-329.

Murthy, Ravi, et al., "Yttrium-90 Microsphere Radioembolotherapy of Hepatic Metastic Neuroendocrine Carcinomas after Heptatic Arterial Embolization", Journal of Vascular and Interventional Radiology, VA, Jan. 8, 2008, pp. 145-151.

Salem, Riad, et al., "Radioembolization with <90> Yttrium Microspheres: A State-of-the-Art Brachytherapy Treatment for Primary and Secondary Liver Malignancies", Journal of Fascular and Interventional Radiology, VA, Sep. 1, 2006, pp. 1425-1439.

Sangro, Bruno, et al., "Radioembolization Using 90Y-resin Microspheres for Pations and Advanced Hepatocellular Carcinoma", International Journal of Radiation: Oncology Biology Physics, Peramon Press, USA, vol. 66, No. 3, Nov. 1, 2006, pp. 792-800.

Yin, Haiqing, et al., "Polymersom Formation from AB2 Type 3-Miktoarm Star Copolymers", Macromolecules, 42, 2009, pp. 7456-7464.

\* cited by examiner

BRACHYTHERAPY SEED WITH FAST DISSOLVING MATRIX FOR OPTIMAL DELIVERY OF RADIONUCLIDES TO CANCER TISSUE

CROSS REFERENCE TO RELATED APPLICATION

This application is a continuation of U.S. patent application Ser. No. 12/552,190 which was filed on Sep. 1, 2009, which is a continuation-in-part of U.S. patent application Ser. No. 12/202,954 filed Sep. 2, 2008, the entirety of each of which are incorporated by reference herein.

FIELD OF THE INVENTION

The present invention relates to therapeutic radiology. More particularly, the present invention is directed to radioactive materials contained in polymers for use in therapeutic applications known as brachytherapy.

BACKGROUND OF THE INVENTION

Treatment of cancerous tissue by exposure to radiation-emitting material is now a well established and accepted practice. Generally, the aims of such a practice include targeting exposure of radiation to the tissue surrounding or adjacent to a radiation source while keeping the radiation effects on neighboring healthy tissue to a minimum. A major advantage of this form of treatment is that it concentrates the emitted radiation at the site where the treatment is needed, e.g. within or adjacent to a tumor, while keeping the amount of radiation transmitted to the healthy tissue far below what it otherwise would be if the radiation were beamed into the body from an external source, using other forms of teletherapy.

Prior art forms of brachytherapy typically include various processes such as placing the source(s) typically small metallic capsules, approximately 4.5 mm long and 0.8 mm in diameter, called seeds containing a radiation sources such as iodine-125, cesium-131, or palladium-103, which are placed within the tissue to be treated, i.e. interstitial therapy. In various embodiments of the construction, the capsule is typically designed to allow the rapid and facile insertion of the seed into the organ or body part being treated, with minimal trauma to the targeted and surrounding tissues. These devices are many times inserted into the body percutaneously using a hollow needle which is preloaded with the desired number of therapy seeds. When the needle is in the desired location in the tissue, a stylet is used to hold the seeds in place while the needle is withdrawn from around them, leaving the seeds in the desired location. The use of such small radiation sources is a common way of practicing interstitial brachytherapy.

In many such methods it is typically considered necessary and in some cases crucial to enclose the radioactive material with an encapsulating material so as to contain the radioactive material and preventing it from becoming systemically distributed within the patient or escaping into the environment where it could contaminate medical personnel, medical facilities or the general environment. Various types of encapsulating devices and materials have been utilized and are presently contemplated. Typically these materials contain the radioactive material while allowing photon radiation (Auger x-rays) to irradiate cancerous tissues while the radioactive source decays to negligible activity. Typically, the metallic seed remains permanently implanted. A further polymer embodiment containing the radioactive source may gradually dissolve in the body after the radioactive source has decayed to negligible activity.

Another major drawback for metal-encapsulated seeds is that the encapsulating metal absorbs a significant fraction of the low-energy beta and photon radiation emitted by the contained radioisotope, for example about 14% of the iodine-125 x-rays and 40% of the palladium-103 x-rays are absorbed in the encapsulating metal in the current commercial seeds. As a consequence, to obtain the desired radiation dose rate on the exterior of the seed, an additional amount of relatively costly radioisotope activity must be added to overcome the losses in the encapsulating metal. Also, because it is typically necessary to seal (or weld), the ends of the capsules, the effective thickness of the metal is not the same in all directions resulting in a radiation field around the seed which is not uniform, a fact that complicates treatment planning and raises the possibility of the existence of areas within the treatment volume in which the radiation dose is non-uniform or below that required to kill all tumor cells present.

Thus the current practice of brachytherapy based on the use of discrete encapsulated sources is limited by: the need to associate groups of discrete seeds together by some means so that they can be placed into tissue in a predetermined array and held in that array throughout the therapeutic life of the sources, the need for complex treatment planning that takes into account the discrete nature of the seeds and the shape of the radiation field around each seed with the assumption the field shape around each seed is uniformly the same, the need to add excess radioactivity to compensate for the radiation absorption in the encapsulating metal, and the creation of a nonuniform radiation field around the source because the geometry and effective thickness of the encapsulating metal is not the same in all directions, and the radiation field about a source is not precisely spherical. The present invention as disclosed herein, significantly reduces each of these limitations and furthermore allows a more complete realization of the potential benefits of brachytherapy. The present invention includes a device, method and system for implementing brachytherapy and creating devices for use in such methods and systems. The present invention provides substantial advantages over the devices taught in the prior art.

Additional advantages and novel features of the present invention will be set forth as follows and will be readily apparent from the descriptions and demonstrations set forth herein. Accordingly, the following descriptions of the present invention should be seen as illustrative of the invention and not as limiting in any way.

SUMMARY

The present invention is a method, system and device for treating tumor cells utilizing a resorbable therapy seed comprising microspheres containing alpha or beta emitting radiation source and a resorbable polymer matrix containing the microspheres. In use, these seeds are implanted within the target tissue, such as a prostate carcinoma tumor, and then dissolved so as to release the microspheres so that they are not encumbered by a surrounding, energy-absorbing material. These microspheres then slightly spread within a preselected target area and provide radiation therapy in an amount and at the rate of radioisotope decay according the specific needs and necessities of the users. The configuration of the microspheres, the types of radiation provided and the location and use of these microspheres provide desired localized treatment to target cancer cells while preferentially avoiding undesired damage to surrounding tissue. Because beta radiation is defined by a distinct energy-range cutoff, this method combined with the materials and methods for production of these materials provides a significantly more effective and less expensive therapy alternative than other methods taught in the prior art.

In one embodiment of the invention the resorbable therapy seed contains a plurality of microspheres preferably of a generally uniform size, and having a diameter of less than 50 microns. While these preferred descriptions are provided it is to be distinctly understood that that the invention is not limited thereto but may be variously alternatively embodied according the respective needs and necessities of the individual user. Each of these individual microspheres contains a beta particle emitting material such as yttrium-90 preferably bound up in an insoluble chemical form. While yttrium-90 has been provided as an example of one material, it is to be distinctly understood that the invention is not limited thereto but may be variously embodied and configured to include a variety of materials including but not limited to phosphorus-32, copper-64, copper-67, iodine-131, lutetium-177, samarium-153, holmium-166, rhenium-186, and rhenium-188. It also includes the alpha-emitters that are usually considered for interstitial radiation therapy, including but not limited to actinium-225, bismuth-213, bismuth-212, thorium-227, radium-223, astatine-211, and terbium-149. This chemical binding of radioisotope within an insoluble form prevents dissolution and release of the radioactive material in body fluids leading to translocation to other parts of the body where such radiation is not desired. A colloid form of binding while not required is preferable.

This beta- or alpha-emitting material is then encapsulated by a fast-resorbable polymer that acts to give physical form and rigidity to the brachytherapy seed, enable surgical placement, and restrain the radioactive material in a desired position and location. In addition to these microspheres, the resorbable seeds of the present invention also contain an imaging material. Various examples of imaging materials may be utilized including but not limited to metallic, preferably gold, particles. Preferably, these microspheres and these imaging materials are mixed within a resorbable polymer matrix that holds the materials together but can respond, after surgical delivery, to various stimuli such as temperature, pH, ultrasonic energy, body fluid characteristics and other influences which increase polymer dissolution rates. This combination can then be pressed or extruded into a shape, preferably rods and then and cut into individual seeds of a particular preselected size. While in some applications the geometry of the particular seed is that of a cylinder having dimensions appropriate for the use of most typical implantation tools, it is to be distinctly understood that the invention not limited thereto but that a variety of other sizes, shapes and dimensions are also contemplated and may be utilized according to the needs and necessities of the user. In particular it is contemplated that generally flat or slightly convex seeds in any of a variety of geometries could be die cut from a flat thin sheet of material may have various useful applications depending upon a particular embodiment. Individual seeds can then be coated with a preferably thin, outer coating so as to provide particular advantages consistent with the needs and necessities of the user.

Preferably, the resorbable therapy seed of the present invention provides a therapeutic index greater than 1.0, and has an effective therapy range that is limited by the range of beta- or alpha-particles in the seed or target tissue (approximately 1.1 cm for yttrium-90) to limit therapy doses to target tissues within this range and protect normal tissue outside of this range from undesirable radiation effects. With these seeds, the method of the present invention can then be performed. In one embodiment of the invention the method comprises the steps of implanting a resorbable therapy seed such as those described above within a preselected tumor or at a preselected location. Once surgically placed, if desired, imaging of the location of the seed can be accomplished. After the seed has been placed, it is rapidly dissolved through any of a variety of ways depending upon the particular material that the polymer matrix is composed of. Thus the dissolution of his material may take place through ultrasonic energy, reaction with the internal temperature of the body, reaction with a body fluid or any of a variety of other ways. Once the seed polymer encapsulation has been appropriately placed and dissolved, the radioactive microspheres are appropriately released within the target cancer. These microspheres generally remain in place and the beta- or alpha-particles from radioactive emissions from the microspheres are appropriately delivered to the target tissues.

The present invention provides a variety of additional advantages over the prior art. These include but are not limited to better radiation quality for tumor cell killing, a better therapeutic index by reducing the dose to nearby normal tissues, and therefore the ability to treat tumors at higher doses than is taught in the prior art, lower cost for materials and preparation, resorbable seed materials dissolve into the body rather than leaving metal pieces in the body, the provision of an outer thin coating that can be variously configured for alternative embodiments and modalities, the ability of the seed to be degraded by ultrasound, and the prevention of unintended migration of the beta emitting material throughout the body.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way. Various advantages and novel features of the present invention are described herein and will become further readily apparent to those skilled in this art from the following detailed description. In the preceding and following descriptions shown and described only the preferred embodiment of the invention, by way of illustration of the best mode contemplated for carrying out the invention. As will be realized, the invention is capable of modification in various respects without departing from the invention. Accordingly, the drawings and description of the embodiments set forth hereafter are to be regarded as illustrative in nature, and not as restrictive.

DETAILED DESCRIPTION OF THE INVENTION

The following description includes the preferred mode of one embodiment of the present invention. It will be clear from this description of the invention that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Figure 1:
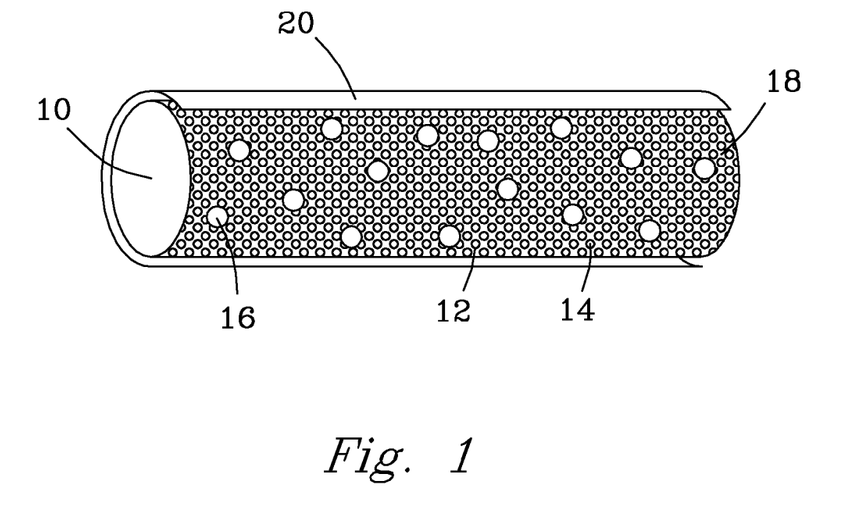
FIG. 1 is a cut-away view of a first embodiment of the device of the present invention.
Figure 2A:
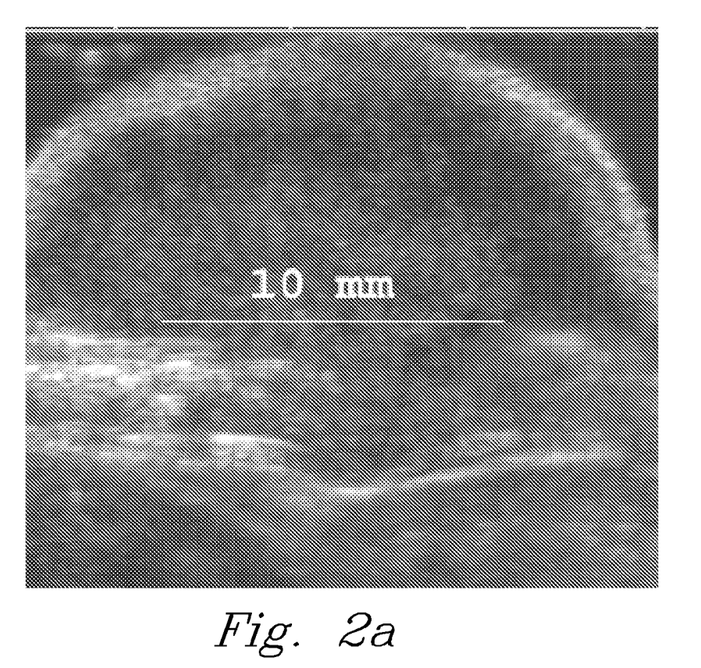
FIG. 2a is a photograph of a tumor mass without implanted marker spheres.
Figure 2B:
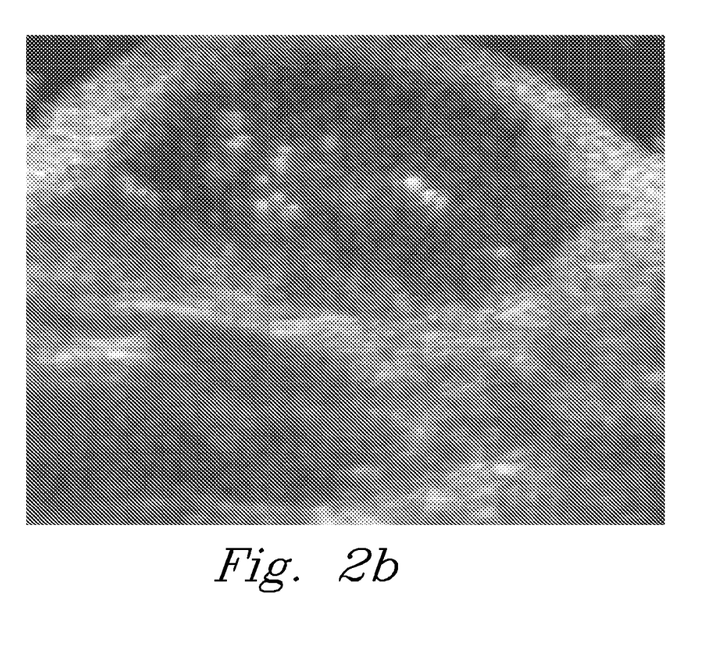
FIG. 2b shows directly injected marker spheres in the tumor, imaged by ultrasound to demonstrate marker imageability.
Figure 3A:
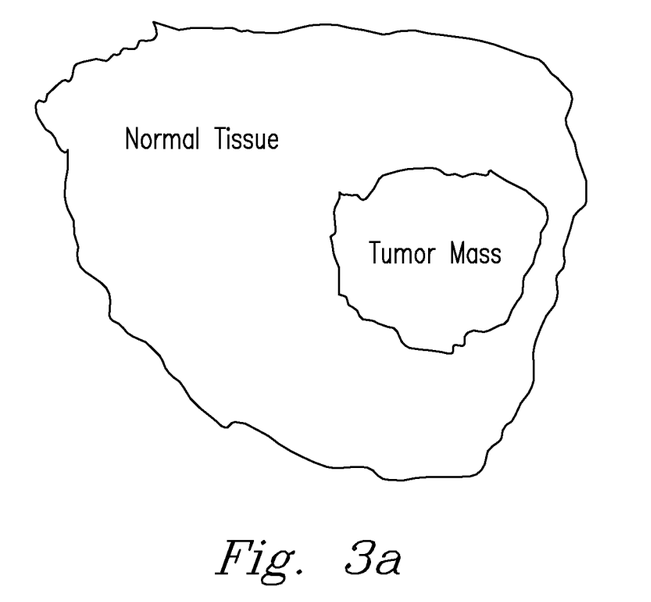
FIG. 3a shows a hypothetical tumor mass within a hypothetical normal mass of tissue.
Figure 3B:
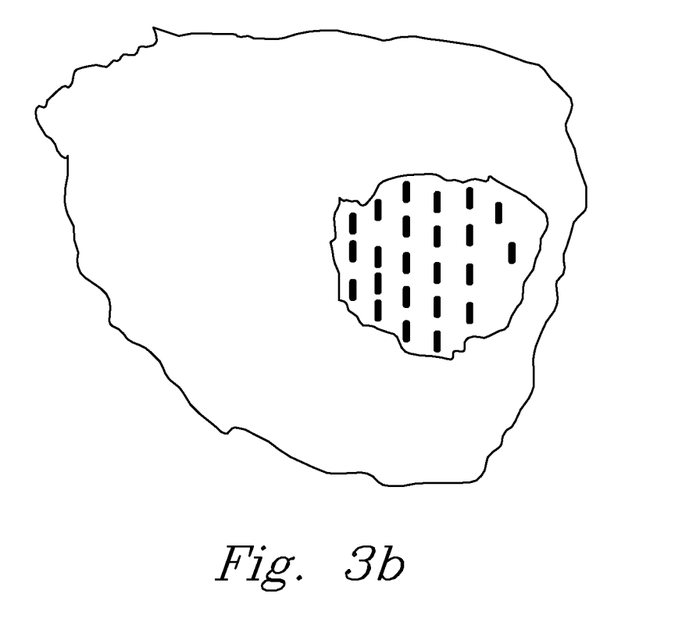
FIG. 3b shows the potential placement of resorbable seeds within the hypothetical tumor mass.
Figure 3C:
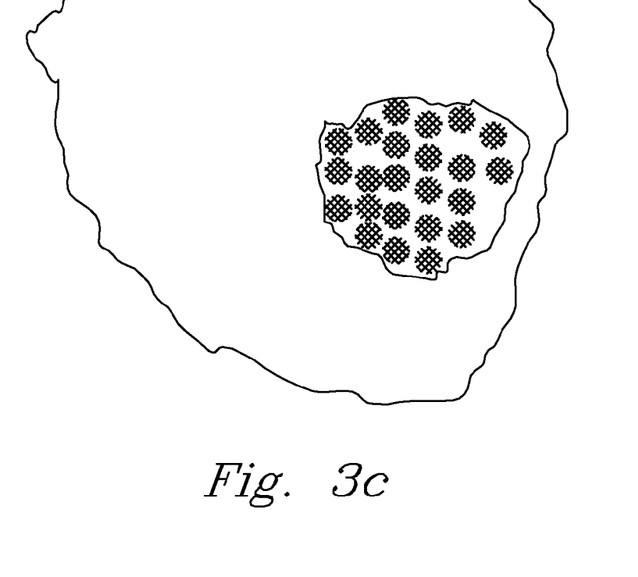
FIG. 3c shows the redistribution of radioactive microspheres after rapid dissolution of the polymer matrix
Figure 3D:
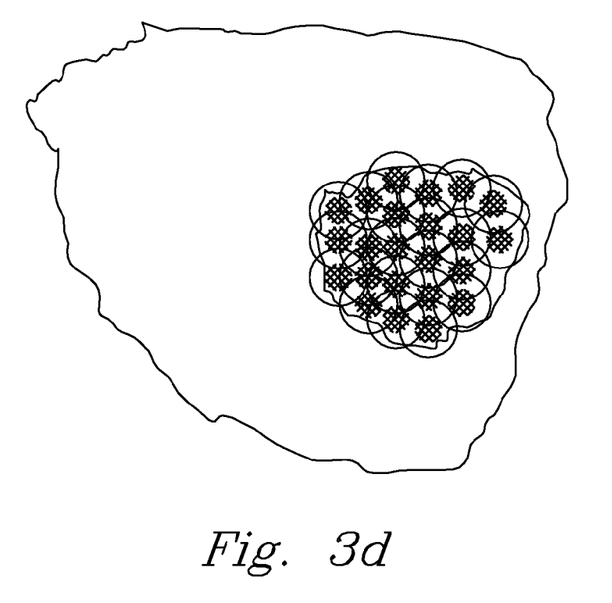
FIG. 3d shows the effective high radiation field around each grouping of radioactive microspheres with sparing of most of the normal tissue.

FIGS. 1-3 show various views and embodiments of the present invention and its implementation. Referring now to FIG. 1, one embodiment of the device of the present invention is shown. In this embodiment of the invention, the present invention is a bioresorbable, fast-dissolving brachytherapy seed 10. In this embodiment this seed 10 is configured to resemble traditional generally cylindrical brachytherapy seeds (generally having an overall diameter of about 1 mm or less and an overall length of about 5 mm or less). This seed contains a plurality of microspheres 12. Each of these microspheres 12 contain a beta particle radiation source 14 which is preferably insolubilized in a colloid formulation so as to prevent the undesired dissolution and movement of these sources away from a desired location after surgical implantation. In this preferred embodiment, an imaging marker 16 consisting of metallic markers are also located within the polymer matrix 18 together with the beta particle microspheres 12 are held within a polymer matrix 18. This polymer matrix 18 is configured to dissolve quickly when subjected to a preselected set of conditions.

Once the seed 10 has been placed and the polymer matrix 18 has been dissolved, the imaging material markers 16 and the beta particle containing microspheres 12 migrate to a designated location. The portions of the microsphere 12 that contain the radiation emissions are removed and release of radiation energy within the tumor takes place. This allows the radioactive material from inside the seed 10 to partially redistribute within the tumor. In one embodiment, the radioactive source is the beta-emitter yttrium-90, in an insoluble form (phosphate) or colloid, to ensure that the radioactive material does not dissolve in body fluids and redistribute widely throughout the body after release from the resorbable or fast-dissolving seed matrix material 18. This allows the radioactive source 14 to remain in the tumor for localized radiation therapy.

In this preferred embodiment of the invention, the seed 10 is administered as a solid cylinder by conventional surgical (intraoperative) seed-placement mechanisms and grids. The seed 10 also contains imageable markers 16 to allow the surgeon placing the seed to visualize seed placement within the tumor using ultrasound, magnetic resonance imaging, CT-imaging, or fluoroscopy. The fast-dissolving matrix 18 allows beta-emitters to be used with greater flexibility and energy-delivery efficiency than if the radionuclide were to be contained within a slow-dissolving polymer or metallic (non-resorbable) seed exterior. Use of beta- or alpha-emitting radionuclides with well-defined range and cut-off distance enables a higher radiation absorbed dose to be delivered to tumors, relative to conventional seed brachytherapy using Auger-electron emitters, without exceeding the normal tissue tolerance of surrounding normal tissues and organs for improved tumor-irradiation efficacy.

The embodiment of the invention described herein allows delivery of the encased radioactive source material to the tumor without loss by contamination prior to delivery, protects hospital workers and the patient from loose contamination, or spread into the environment as radioactive contamination, rapidly dissolves in the tumor after surgical placement, and can be easily formable into a desired size, (In the preferred embodiment this is generally a cylinder shape with a diameter of 0.5 to 0.8 mm and a length of about 4.5 to 5 mm). Two different kinds of technology will be employed for extruding or pressing the seed, however it is to be distinctly understood that the invention is not limited thereto but may be variously embodied according to the needs and necessities of a user.

In one method of preparing the seeds, a wet granule preparation process is utilized. In this embodiment all seed materials, including the radioactive source 14, gold markers 16, and rapidly dissolving excipients 18-mixed together with proper solvents are combined for form a mixture. This mixture is then extruded against a desired size sieve and dried in an oven. These extruded sections can then be cut into seeds of a desired size and if desired coated with a coating material 20. The second method for preparing the brachytherapy granules involves directly compressing the seeds from the dry mixture of radiation source 14, imaging materials 16, and polymer matrix 18, using a mechanical, high-force tablet press. This direct compression method is generally preferred, however if the mixed material is powder and difficult to prepare to make granules by direct compression method, the previously described wet method will be the preferred alternative.

In this embodiment of the present invention the matrix 18 containing the radioactive source 14 and marker material 16 dissolves quickly (minutes to hours) to release the radioactive source 14 in tumor tissue after placement. This is dramatically shorter than prior art seeds which typically require weeks to months to dissolve. The dissolution of the polymer matrix 18 can be variously configured according to the needs of the user. Various types of stimuli can be utilized to accomplish this dissolution including but not limited to heat, ultrasound, body fluid, and other stimuli. Similar types of stimuli can be utilized to affect the coating 20 of the seed.

In one embodiment of the invention the polymer matrix 18 is one that disintegrates rapidly in water or body fluids. In another embodiment of the invention the polymer-matrix 18 is a temperature-induced or thermally stimulated, rapidly dissolving system. Various polymer materials may be included in these matrices depending upon the particular needs of the individuals involved. While various materials can be utilized, typical polymers such as PLA (poly lactic acid) and PLGA (copoly lactic acid/glycolic acid are envisioned. Typical PLA and PLGA biodegradable polymers have molecular weights ranging from 5,000 to 100,000. They are also available as mixtures of PLA and PLGA, for example 75%/25% or 50%/50%. They may constitute 0.5 percent to 5 percent of the seed. When pressed with sorbitol, the major inert part of the seed, the polymers bind the sorbitol into a hard form or shape, and also provide a protective coating about the sorbitol. The sorbitol is a standard inert pharmaceutical additive for pills. In such embodiments a beta-particle-emitting radionuclide, such as yttrium-90, rhenium-186, rhenium-188, or lutetium-177 is utilized as insoluble colloid or microsphere 12. In addition, alpha emitters such as actinium-225, bismuth-213, bismuth-212, thorium-227, radium-223, astatine-211, or terbium-149 could also be used as the active agent. These seeds 10 also may contain markers such as radioactive gold-198 or gold-197, or with stable gold markers, as well as anti-inflammatory agents such as ibuprofen, florabioprofen, aspirin, acetaminophen, endocen, toridol, voltren, telecten, and ketoprofen. The polymers, sorbitol, active agents, markers and anti-inflammatory agents would be produced or prepared under good manufacturing practices (controlled for sterility and apyrogenicity). These formulations will serve as brachytherapy and position-monitoring source materials for imaging—for example by ultrasound or gamma-camera imaging system common to nuclear medicine clinics. In some other embodiments and applications dissolution of the polymer matrices may be enhanced by the user of 1 to 3 MHz ultrasound on the site of tumor after localizing the seeds 10 to enhance the break-up and dissolution of the seed matrix.

In experiments embodiments of the present invention the microspheres of the present invention were included in tablets containing sorbitol and either a biodegradable or non biodegradable polymer. While various materials can be utilized, examples of various polymers such as PLA (poly lactic acid) and PLGA (copoly lactic acid/glycolic acid are envisioned. The exact concentration of and size of the polymer were variously altered to affect the rate of dissolution of the material. In the experiments it was found that tablets containing the inert ingredient sorbitol coated with a 2 percent (30,000 MW) biodegradable polymers such as PLA (poly lactic acid) or combinations of poly lactic acid and PLGA (copoly lactic acid/glycolic acid) dissolved most quickly in water, while another formulation having 0.5% of the same polymer absorbed most quickly in tissue studies. Tablets using varying concentrations of less biodegradable materials such as the ammonio methacrylate copolymers sold under the tradename EUDRAGIT RL and EUDRAGIT RZ dissolved much more slowly. Depending upon the desired characteristics to be imparted to the particular tablet, the type, concentration, formulation and configuration of the particular ingredients may be variously and appropriately modified according to the needs and necessities of the user.

In one preferred formulation a water or body fluid dissolvable polymer matrix 18 includes crospovidone (N-vinyl-2-pyrrolidone) sold under the trade name Polyplasdone®XL-10, International Specialty Products Wayne, N.J. USA. In addition to this material, a variety of other types of materials may also be utilized to bring about a similar result. Examples of such other materials include but are not limited to polyvinylpyrrolidone, starch, alginic acid, formaldehyde, calcium carboxymethyl cellulose, sodium starch glycolate, and sodium carboxymethyl cellulose.

In addition to these materials, cellulose derivatives may also serve as an excipient. These include hydroxypropylmethylcellulose, such as those sold under the trade names "TC-5E", "Metolose 90", "Metolose 65SH", trade names; produced by Shin-Etsu Chemical Co., Ltd. Tokyo, Japan), hydroxypropylcellulose (for example, "Nisso HPC", trade name; produced by Nippon Soda Co., Ltd. Tokyo, Japan), methyl cellulose (for example, "Metolose SM", trade name; produced by Shin-Etsu Chemical Co., Ltd., Tokyo, Japan), and hydroxyethylcellulose ("NATROSOL", trade name; produced by Hercules Japan, Ltd., Tokyo Japan). More preferred is hydroxypropylmethylcellulose.

Various soluble diluents agents may be required for the wet prepping process of the invention these include but are not limited to a soluble diluent with binding properties that consist of a polyol having less than 13 carbon atoms and being either in the form of the directly compressible product with an average particle diameter of 100 to 500 micrometers, or in the form of a dry powder with an average particle diameter of less than 100 micrometers. Preferably, this polyol is selected from the group comprising mannitol, xylitol, sorbitol and maltitol. In addition to these materials, the addition of a lubricant used in the fast release formulation may also be utilized. Examples of such lubricants include conventional lubricants, such as magnesium stearate, sodium dodecyl sulfate. Generally, it is preferred that the lubricant be water soluble. Hence, the preferred lubricant is sodium dodecyl sulfate in an amount ranging from about 1 to 3 percent.

In a second embodiment of the present invention the polymer based matrix is a temperature-sensitive rapid disintegrating formulation. Temperature-sensitive, rapid-dissolving formulations, are preferably made from materials that are in a generally solid state at room temperature and provide sufficient rigidity to allow injection of a seed made from such material into the tumor tissue. This material preferably would then dissolve in the tumor site at 37-42 degrees C. Ultrasound treatment can be used to increase local material temperature. Formulation matrices can be oleophilic bases and/or water-soluble bases, and can be used in combination. Examples of oleophilic bases include cacao butter, lanolin fat and hard fats. Examples of the hard fats include: Witepsol, tradename, manufactured by Huls Inc.), Suppocire, tradename, (manufactured by Gattefosse Inc.), lsocacao, tradename, (manufactured by Kao Corp.), and tradename, Pharmasol (manufactured by NOF Corp.), etc.

In most preferred embodiments of the present invention the beta- or alpha-emitting radiation source has a generally short half-life (less than 60 days, and preferably less than 9 days). More specifically, in certain cases the radioisotope is selected from the group of yttrium-90, phosphorus-32, copper-64, copper-67, iodine-131, lutetium-177, samarium-153, holmium-166, rhenium-186, rhenium-188, and combinations thereof. Beta particles have short path length in tissue, which indicates minimal irradiation of surrounding normal tissue. In addition, these beta emitting radiation sources are generally confined to a specific target tissue. Alpha particle ranges are even shorter (typically 40 to 80 micrometers) in tissue.

The purpose of the radioactive confine is to minimize or prevent migration of the radioisotope to healthy tissue areas. The radioisotope may be confined, for example, by chelators or complexing agents, capsules, and combinations thereof. Examples of useful isotope/chelator combinations are, for example, yttrium-90 with 1,4,7,10-tetraazacyclododecane-N,N',N'',N'''-tetraacetic acid (DOTA), derivatives of DOTA. In addition to these materials insoluble salts such as 90-yttrium phosphate may also be utilized. It is preferred that particles of the insoluble salt are hydrothermally synthesized in solution as the disperse phase of a colloid. As used herein a colloid is a chemical system composed of a continuous medium (continuous phase) throughout which are distributed small particles, for example about 0.0001 micrometer to about 3 micrometer in size (the disperse phase). Hydrothermal synthesis refers to the synthesis of products by reacting reagents in solution at temperatures and/or pressures above ambient temperature and/or pressure, such as by performing the reaction in a sealed vessel (generally known as a hydrothermal bomb) that may also be heated. The hydrothermal bomb may include a liner in which reagents are reacted so that the bomb can more easily be reused.

Hydrothermal synthesis of insoluble salt particles containing the radioactive agent allows for control of particle shape and/or size. While uniform size and shape are not required, these characteristics can aid in determining the amount of radioactive agent to administer to achieve a particular dose of radiation to tissue in vivo. That is the more uniform the particles are in size and/or shape the more consistent the radiation doses for a particular amount of particles because similar sized and/or shaped particles provide similar amounts of radiation.

Certain embodiments of hydrothermal syntheses of insoluble salt radioactive therapeutic agents, such as YPO.sub.4 particles, include a complexing agent, such as a compound comprising ethylene diamine tetraacetic acid (EDTA), to bind metal cations, such as Y.sup.3+, in solution, allowing the cations to exceed the saturation concentration without significant precipitation of the salt. During hydrothermal synthesis the EDTA releases the cations to react with anions, such as YPO.sub.4.sup.3−, to form particles. In certain embodiments the particles formed are colloidal, that is, the particles form a disperse phase of a colloid in the continuous phase of the solution.

In certain embodiments, colloids including YPO.sub.4 particles as the disperse phase are synthesized using EDTA, an yttrium (Y) source, and a phosphate (PO.sub.4) source, all reacted in a hydrothermal bomb. Preferably the seeds in the preferred embodiment also include an imaging material such as a metallic marking material. In one preferred embodiment gold particles were utilized as an ultrasound marker or contrast agent. The presence of these marking materials allows placement of the seeds in the tissue to be verified and monitored through the use of ultrasound imaging, magnetic resonance imaging, x-ray fluoroscopy, or other standard medical imaging modality. Examples of such images are shown in FIG. 2a-b. FIG. 2a shows a tumor ultrasound images before marker placement, and FIG. 2b shows a tumor ultrasound image after placement of spherical markers into a mouse tumor. Thus this material when combined with the seed matrix, could render the brachytherapy seeds sufficiently imageable via ultrasound for practical application as an aid to surgical placement in tumor tissue. The images also allow the surgeon to verify that the seed are correctly place in the target tissue.

While ultrasound imaging is described herein it is to be distinctly understood that the imaging step is not limited thereto but may be variously embodied and configured according to the needs and necessities of the user. If necessary, ultrasound may also be used to enhance matrix dissolution. This can be done utilizing a tissue-warming device such as a Omnisound 3000 commercialized ultrasound machine with 1 MHz and 3 MHz signals, that modify the power density, duty cycle, and wave irradiation time to optimize the brachytherapy seed dissolution.

In one example of the present invention, seeds 10 as described above are implanted into a selected portion of tumor tissue. The tumor is preferably imaged to verify placement of the seeds in the desired location. After this imaging has taken place, the seeds are dissolved and microparticles that contain the beta- or alpha-emitting source are then released to provide therapeutic radiation to the tumor to destroy the unwanted tumor tissue. This method provides several advantages. First, this method provides a user the ability to use inexpensive materials as the seed matrix, radioisotope, and markers. Second, this less expensive seed has the ability to deliver higher localized radiation doses to radiation-insensitive solid tumors (which could include cancers of the liver, pancreas, brain, kidney, head and neck, prostate, colon, and others, or solid tumors that are not resectable and that must be treated effectively without surgical removal, such as those that may surround major blood vessels, the vocal chords or spinal column nerves. The present invention provides an ability to use radioisotopes other than the more common Auger-electron-emitters traditionally used in seed brachytherapy, such as iodine-125, paladium-103, and cesium-131, which are all relatively expensive to produce. The present invention also provides the ability to deliver more locally intense radiation doses to tumor tissues than achieved using the Auger-electron emitters mentioned above.

While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

What is claimed is:

1. A brachytherapy seed consisting essentially of a mixture of a crystalline radioisotope and individual particles of sorbitol coated with biodegradable polymer.

2. The brachytherapy seed of claim 1 wherein the radioisotope is a beta-particle-emitting radionuclide.

3. The brachytherapy seed of claim 1 wherein the radioisotope is one of yttrium-90, rhenium-186, rhenium-188, or lutetium-177.

4. The brachytherapy seed of claim 1 wherein the radioisotope is an alpha-particle-emitting radionuclide.

5. The brachytherapy seed of claim 1 wherein the radioisotope is one of actinium-225, bismuth-213, bismuth-212, thorium-227, radium-223, astatine-211, or terbium-149.

6. The brachytherapy seed of claim 1 further consisting of at least one marker.

7. The brachytherapy seed of claim 6 wherein the at least one marker comprises radio opaque material.

8. The brachytherapy seed of claim 1 further consisting essentially of an anti-inflammatory agent.

9. The brachytherapy seed of claim 1 wherein the biodegradable polymer comprises one or both of PLA and PLGA.

10. The brachytherapy seed of claim 1 wherein the biodegradable polymer has a molecular weight ranging from 5,000 to 100,000.

11. The brachytherapy seed of claim 1 wherein the biodegradable polymer comprises both PLA and PLGA, the ratio of PLA to PLGA being from about 3:1 to about 1:1.

12. The brachytherapy seed of claim 1 wherein the biodegradable polymer is provided to constitute from 0.5 to 5 percent of the seed.

13. A method for preparing a brachytherapy seed, the method comprising:
   providing a structure comprising a crystalline radioisotope;
   providing a mixture of particles, individual ones of the particles comprising sorbitol coated with a biodegradable polymer; and
   pressing the mixture of particles about the structure to form a brachytherapy seed consisting essentially of a mixture of the crystalline radioisotope and the particles.

14. The method of claim 13 wherein the providing the mixture of particles comprises binding the sorbitol with the biodegradable polymer to form the particles.

15. The method of claim 13 wherein the biodegradable polymer comprises one or both of PLA and PLGA.

16. The method of claim 13 wherein the biodegradable polymer has a molecular weight ranging from 5,000 to 100,000.

17. The method of claim 13 wherein the biodegradable polymer comprises both PLA and PLGA, the ratio of PLA to PLGA being from about 3:1 to about 1:1.

18. The method of claim 13 wherein the biodegradable polymer is provided to constitute from 0.5 to 5 percent of the seed.

19. The method of claim 13 wherein the biodegradable polymer is natural.

* * * * *